(12) United States Patent
Pamichev et al.

(10) Patent No.: US 12,305,631 B2
(45) Date of Patent: May 20, 2025

(54) HEAT EXCHANGE SYSTEM FOR PATIENT TEMPERATURE CONTROL WITH EASY LOADING HIGH PERFORMANCE PERISTALTIC PUMP

(71) Applicant: ZOLL Circulation, Inc., San Jose, CA (US)

(72) Inventors: Christo Petrov Pamichev, Cupertino, CA (US); Jeremy Thomas Dabrowiak, Santa Clara, CA (US)

(73) Assignee: ZOLL Circulation, Inc., San Jose, CA (US)

( * ) Notice: Subject to any disclaimer, the term of this patent is extended or adjusted under 35 U.S.C. 154(b) by 113 days.

(21) Appl. No.: 17/662,240

(22) Filed: May 6, 2022

(65) Prior Publication Data

US 2022/0268269 A1 Aug. 25, 2022

Related U.S. Application Data

(63) Continuation of application No. 14/676,682, filed on Apr. 1, 2015, now Pat. No. 11,359,620.

(51) Int. Cl.
*F04B 43/12* (2006.01)
*A61F 7/00* (2006.01)
(Continued)

(52) U.S. Cl.
CPC ............ *F04B 43/1261* (2013.01); *A61F 7/00* (2013.01); *A61F 7/0085* (2013.01); *A61F 7/12* (2013.01);
(Continued)

(58) Field of Classification Search
CPC .............. F04B 43/1253; F04B 43/1284; F04B 43/1276; F04B 43/12; F04B 2201/1208;
(Continued)

(56) References Cited

U.S. PATENT DOCUMENTS 1,459,112 A 6/1923 Mehl
1,726,761 A 9/1929 Palmer
(Continued)

FOREIGN PATENT DOCUMENTS

CN 1829860 9/2006
CN 101090685 12/2007
(Continued)

OTHER PUBLICATIONS

F.W. Behmann, E. Bontke, "Die Regelung der Warmebildung bei kunsticher Hypothermi", Pffugers Archiv. Bd 266, S. 406-421, 1958.
(Continued)

*Primary Examiner* — Peter J Bertheaud
(74) *Attorney, Agent, or Firm* — ZOLL Circulation, Inc.

(57) ABSTRACT

A peristaltic pump has an arcuate raceway with a partially concave inner surface extending through an arc of at least one hundred eighty degrees (180°). The arc defines a midpoint, and a rotor faces the inner surface of the raceway and is both rotatable relative to the raceway and translationally movable relative to the raceway between a pump position, wherein the rotor is spaced from the midpoint a first distance, and a tube load position, wherein the rotor is spaced from the midpoint a second distance greater than the first distance. A rotor motor is coupled to the rotor to rotate the rotor and rollers arranged on the rotor to contact tubing disposed between the rotor and the raceway when the rotor is in the pump position. A loading motor moves the rotor toward and away from the raceway.

21 Claims, 8 Drawing Sheets

(51) Int. Cl.
*A61F 7/12* (2006.01)
*A61M 1/00* (2006.01)
*A61M 3/02* (2006.01)
*A61M 5/142* (2006.01)

(52) U.S. Cl.
CPC ............ *A61M 1/72* (2021.05); *A61M 3/0201* (2021.05); *A61M 3/0202* (2021.05); *A61M 5/14232* (2013.01); *F04B 43/12* (2013.01); *F04B 43/1253* (2013.01); *F04B 43/1276* (2013.01); *F04B 43/1284* (2013.01); *A61F 2007/0054* (2013.01); *A61F 2007/126* (2013.01); *A61M 2205/12* (2013.01); *F04B 2201/1208* (2013.01)

(58) Field of Classification Search
CPC .......... A61M 5/14232; A61M 2205/12; A61M 1/72; A61M 3/0201; A61M 3/0202; A61F 2007/0054; A61F 7/12; A61F 2007/126; A61F 7/0085; A61F 7/00; A61F 2007/12
See application file for complete search history.

(56) References Cited

U.S. PATENT DOCUMENTS

| | | |
|---|---|---|
| 1,857,031 A | 5/1932 | Schaffer |
| 2,223,688 A | 12/1940 | Otoo |
| 2,663,030 A | 12/1953 | Dahlberg |
| 2,673,987 A | 4/1954 | Upshaw et al. |
| 2,696,173 A | 12/1954 | Thormod |
| 2,893,324 A | 7/1959 | Isreeli |
| 2,987,004 A | 6/1961 | Murray |
| 3,140,716 A | 7/1964 | Harrison et al. |
| 3,225,191 A | 12/1965 | Calhoun |
| 3,228,465 A | 1/1966 | Vadot |
| 3,369,549 A | 2/1968 | Armao |
| 3,425,419 A | 2/1969 | Dato |
| 3,504,574 A | 4/1970 | Okabe |
| 3,504,674 A | 4/1970 | Swenson et al. |
| 3,726,259 A | 4/1973 | Graves |
| 3,726,269 A | 4/1973 | Webster |
| 3,744,555 A | 7/1973 | Fletcher et al. |
| 3,744,556 A | 7/1973 | Church |
| 3,751,077 A | 8/1973 | Hiszpanski |
| 3,834,396 A | 9/1974 | Foster et al. |
| 3,937,224 A | 2/1976 | Uecker |
| 3,945,063 A | 3/1976 | Matsuura |
| 4,038,519 A | 7/1977 | Foucras |
| 4,065,264 A | 12/1977 | Lewin |
| 4,103,511 A | 8/1978 | Kress et al. |
| 4,126,132 A | 11/1978 | Portner et al. |
| 4,153,048 A | 5/1979 | Magrini |
| 4,173,228 A | 11/1979 | Childress et al. |
| 4,181,132 A | 1/1980 | Parks |
| 4,181,245 A | 1/1980 | Garrett et al. |
| 4,231,707 A | 11/1980 | Tokorozawa |
| 4,259,961 A | 4/1981 | Hood, III |
| 4,298,006 A | 11/1981 | Parks |
| 4,459,468 A | 7/1984 | Bailey |
| 4,532,414 A | 7/1985 | Shah et al. |
| 4,552,516 A | 11/1985 | Stanley |
| 4,554,793 A | 11/1985 | Harding, Jr. |
| 4,558,996 A | 12/1985 | Becker |
| 4,581,017 A | 4/1986 | Sahota |
| 4,638,436 A | 1/1987 | Badger et al. |
| 4,653,987 A | 3/1987 | Tsuji et al. |
| 4,661,094 A | 4/1987 | Simpson |
| 4,665,391 A | 5/1987 | Spani |
| 4,672,962 A | 6/1987 | Hershenson |
| 4,754,752 A | 7/1988 | Ginsburg et al. |
| 4,787,388 A | 11/1988 | Hofmann |
| 4,813,855 A | 3/1989 | Leveen et al. |
| 4,849,196 A | 7/1989 | Yamada et al. |
| 4,852,567 A | 8/1989 | Sinofsky |
| 4,860,744 A | 8/1989 | Johnson et al. |
| 4,869,250 A | 9/1989 | Bitterly |
| 4,906,237 A | 3/1990 | Johansson et al. |
| 4,925,376 A | 5/1990 | Kahler |
| 4,941,475 A | 7/1990 | Williams et al. |
| 4,976,590 A | 12/1990 | Baldwin |
| 5,080,089 A | 1/1992 | Mason et al. |
| 5,092,841 A | 3/1992 | Spears |
| 5,096,393 A | 3/1992 | Van Steenderen |
| 5,103,360 A | 4/1992 | Maeda |
| 5,106,360 A | 4/1992 | Ishiwara et al. |
| 5,174,285 A | 12/1992 | Fontenot |
| 5,192,274 A | 3/1993 | Bierman |
| 5,195,965 A | 3/1993 | Shantha |
| 5,211,631 A | 5/1993 | Sheaff |
| 5,263,925 A | 11/1993 | Gilmore, Jr. et al. |
| 5,269,758 A | 12/1993 | Taheri |
| 5,281,215 A | 1/1994 | Milder |
| 5,304,214 A | 4/1994 | Deford et al. |
| 5,342,301 A | 8/1994 | Saab |
| 5,344,436 A | 9/1994 | Fontenot et al. |
| 5,370,675 A | 12/1994 | Edwards et al. |
| 5,383,856 A | 1/1995 | Bersin |
| 5,387,088 A | 2/1995 | Knapp |
| 5,391,030 A | 2/1995 | Lee |
| 5,403,281 A | 4/1995 | O'Neill et al. |
| 5,433,588 A | 7/1995 | Monk et al. |
| 5,433,740 A | 7/1995 | Yamaguchi |
| 5,437,673 A | 8/1995 | Baust et al. |
| 5,458,639 A | 10/1995 | Tsukashima et al. |
| 5,466,208 A | 11/1995 | Jackson et al. |
| 5,476,368 A | 12/1995 | Rabenau et al. |
| 5,486,207 A | 1/1996 | Mahawili |
| 5,486,208 A | 1/1996 | Ginsburg |
| 5,507,792 A | 4/1996 | Mason et al. |
| 5,531,714 A | 7/1996 | Dahn et al. |
| 5,531,776 A | 7/1996 | Ward et al. |
| 5,549,458 A | 8/1996 | Chapman |
| 5,549,559 A * | 8/1996 | Eshel ...................... A61F 7/123 604/113 |
| 5,624,392 A | 4/1997 | Saab |
| 5,634,907 A | 6/1997 | Rani et al. |
| 5,657,000 A | 8/1997 | Ellingboe |
| 5,676,670 A | 10/1997 | Kim |
| 5,693,344 A | 12/1997 | Knight et al. |
| 5,701,905 A | 12/1997 | Esch |
| 5,706,889 A | 1/1998 | Bach et al. |
| 5,709,564 A | 1/1998 | Yamada et al. |
| 5,709,654 A | 1/1998 | Klatz et al. |
| 5,711,654 A | 1/1998 | Afflerbaugh |
| 5,716,386 A | 2/1998 | Ward et al. |
| 5,730,720 A | 3/1998 | Sites et al. |
| 5,733,319 A | 3/1998 | Neilson et al. |
| 5,737,782 A | 4/1998 | Matsuura et al. |
| 5,746,585 A | 5/1998 | McDunn |
| 5,746,885 A | 5/1998 | Stockwell et al. |
| 5,759,017 A | 6/1998 | Patton et al. |
| 5,776,079 A | 7/1998 | Cope et al. |
| 5,788,647 A | 8/1998 | Eggers |
| 5,803,324 A | 9/1998 | Silberman et al. |
| 5,837,003 A | 11/1998 | Ginsburg |
| 5,857,843 A | 1/1999 | Leason |
| 5,862,675 A | 1/1999 | Scaringe et al. |
| 5,875,282 A | 2/1999 | Jordan et al. |
| 5,879,329 A | 3/1999 | Ginsburg |
| 5,895,418 A | 4/1999 | Saringer |
| 5,908,407 A | 6/1999 | Frazee et al. |
| 5,957,963 A | 9/1999 | Dobak, III |
| 5,980,561 A | 11/1999 | Kolen et al. |
| 5,989,238 A | 11/1999 | Ginsburg |
| 6,019,783 A | 2/2000 | Philips et al. |
| 6,042,559 A | 3/2000 | Dobak, III |
| 6,051,019 A | 4/2000 | Dobak, III |
| 6,059,825 A | 5/2000 | Hobbs et al. |
| 6,096,068 A | 8/2000 | Dobak, III et al. |
| 6,110,139 A | 8/2000 | Loubser |
| 6,110,168 A | 8/2000 | Ginsburg |
| 6,117,065 A | 9/2000 | Hastings et al. |
| 6,117,105 A | 9/2000 | Bresnahan et al. |

(56) References Cited

U.S. PATENT DOCUMENTS

| | | |
|---|---|---|
| 6,124,452 A | 9/2000 | Dimagno |
| 6,126,684 A | 10/2000 | Gobin et al. |
| 6,146,141 A | 11/2000 | Schumann |
| 6,146,411 A | 11/2000 | Noda et al. |
| 6,148,634 A | 11/2000 | Sherwood |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,149,806 A | 11/2000 | Baer |
| 6,165,207 A | 12/2000 | Balding |
| 6,188,930 B1 | 2/2001 | Carson et al. |
| 6,197,045 B1 | 3/2001 | Carson et al. |
| 6,224,624 B1 | 5/2001 | Lasheras |
| 6,231,594 B1 | 5/2001 | Dae et al. |
| 6,231,595 B1 | 5/2001 | Dobak |
| 6,235,048 B1 | 5/2001 | Dobak, III |
| 6,238,428 B1 | 5/2001 | Werneth |
| 6,245,095 B1 | 6/2001 | Dobak, III et al. |
| 6,251,129 B1 | 6/2001 | Dobak, III et al. |
| 6,251,130 B1 | 6/2001 | Dobak, III et al. |
| 6,254,626 B1 | 7/2001 | Dobak, III |
| 6,261,312 B1 | 7/2001 | Dobak, III et al. |
| 6,264,679 B1 | 7/2001 | Keller et al. |
| 6,283,940 B1 | 9/2001 | Mulholland |
| 6,287,326 B1 | 9/2001 | Pecor |
| 6,290,717 B1 | 9/2001 | Philips |
| 6,299,599 B1 | 10/2001 | Pham et al. |
| 6,306,161 B1 | 10/2001 | Ginsburg |
| 6,312,452 B1 | 11/2001 | Dobak, III et al. |
| 6,325,818 B1 | 12/2001 | Werneth |
| 6,338,727 B1 | 1/2002 | Noda et al. |
| 6,364,899 B1 | 4/2002 | Dobak, III |
| 6,368,304 B1 | 4/2002 | Aliberto et al. |
| 6,375,674 B1 | 4/2002 | Carson |
| 6,379,378 B1 | 4/2002 | Werneth et al. |
| 6,383,144 B1 | 5/2002 | Mooney et al. |
| 6,383,210 B1 | 5/2002 | Magers et al. |
| 6,387,326 B1 | 5/2002 | Edwards et al. |
| 6,393,320 B2 | 5/2002 | Lasersohn et al. |
| 6,399,599 B1 | 6/2002 | Albert et al. |
| 6,405,080 B1 | 6/2002 | Lasersohn et al. |
| 6,409,747 B1 | 6/2002 | Gobin et al. |
| 6,416,533 B1 | 7/2002 | Gobin et al. |
| 6,419,643 B1 | 7/2002 | Shimada et al. |
| 6,428,563 B1 | 8/2002 | Keller |
| 6,440,468 B1 | 8/2002 | Quintanilla Almagro et al. |
| 6,450,990 B1 | 9/2002 | Walker et al. |
| 6,461,379 B1 | 10/2002 | Carson et al. |
| 6,464,666 B1 | 10/2002 | Augustine et al. |
| 6,464,716 B1 | 10/2002 | Dobak, III et al. |
| 6,497,721 B2 | 12/2002 | Ginsburg et al. |
| 6,527,798 B2 | 3/2003 | Ginsburg et al. |
| 6,530,946 B1 | 3/2003 | Noda et al. |
| 6,544,282 B1 | 4/2003 | Dae et al. |
| 6,551,309 B1 | 4/2003 | LePivert |
| 6,554,791 B1 | 4/2003 | Cartledge et al. |
| 6,582,387 B2 | 6/2003 | Derek et al. |
| 6,605,106 B2 | 8/2003 | Schwartz |
| 6,610,063 B2 | 8/2003 | Kumar et al. |
| 6,610,083 B2 | 8/2003 | Keller et al. |
| 6,613,280 B2 | 9/2003 | Myrick et al. |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,622,542 B2 | 9/2003 | Derek et al. |
| 6,624,679 B2 | 9/2003 | Tomaiuolo et al. |
| 6,635,076 B1 | 10/2003 | Ginsburg |
| 6,635,079 B2 | 10/2003 | Unsworth et al. |
| 6,645,232 B2 | 11/2003 | Carson |
| 6,648,905 B2 | 11/2003 | Hoglund et al. |
| 6,656,209 B1 | 12/2003 | Ginsburg |
| 6,660,027 B2 | 12/2003 | Gruszecki et al. |
| 6,669,715 B2 | 12/2003 | Hoglund et al. |
| 6,673,098 B1 | 1/2004 | Machold et al. |
| 6,675,835 B2 | 1/2004 | Gerner et al. |
| 6,679,906 B2 | 1/2004 | Hammack et al. |
| 6,685,731 B2 | 2/2004 | Kushnir et al. |
| 6,685,733 B1 | 2/2004 | Dae et al. |
| 6,692,518 B2 | 2/2004 | Carson |
| 6,695,874 B2 | 2/2004 | Machold et al. |
| 6,699,269 B2 | 3/2004 | Khanna |
| 6,706,050 B1 | 3/2004 | Giannadakis |
| 6,706,060 B2 | 3/2004 | Tzeng et al. |
| 6,716,188 B2 | 4/2004 | Noda et al. |
| 6,718,012 B2 | 4/2004 | Ein-Gal |
| 6,719,723 B2 | 4/2004 | Werneth |
| 6,719,779 B2 | 4/2004 | Daoud |
| 6,726,653 B2 | 4/2004 | Noda et al. |
| 6,733,495 B1 | 5/2004 | Bek et al. |
| 6,740,109 B2 | 5/2004 | Dobak, III |
| 6,743,201 B1 | 6/2004 | Doenig et al. |
| 6,764,391 B1 | 7/2004 | Grant et al. |
| 6,774,800 B2 | 8/2004 | Friedman et al. |
| 6,799,063 B2 | 9/2004 | Carson |
| 6,799,342 B1 | 10/2004 | Jarmon |
| 6,802,855 B2 | 10/2004 | Ellingboe et al. |
| 6,818,012 B2 | 11/2004 | Ellingboe |
| 6,827,728 B2 | 12/2004 | Ellingboe et al. |
| 6,843,099 B2 | 1/2005 | Daw et al. |
| 6,843,800 B1 | 1/2005 | Dobak, III |
| 6,878,156 B1 | 4/2005 | Noda |
| 6,887,263 B2 | 5/2005 | Bleam et al. |
| 6,890,347 B2 | 5/2005 | Machold et al. |
| 6,890,893 B2 | 5/2005 | Datta |
| 6,893,419 B2 | 5/2005 | Noda et al. |
| 6,959,758 B2 | 11/2005 | Hughes et al. |
| 6,969,399 B2 | 11/2005 | Schock et al. |
| 6,974,435 B2 | 12/2005 | Daw et al. |
| 6,997,942 B2 | 2/2006 | Machold et al. |
| 7,004,960 B2 | 2/2006 | Daoud |
| 7,013,703 B2 | 3/2006 | Derek et al. |
| 7,028,692 B2 | 4/2006 | Sterman et al. |
| 7,070,612 B1 | 7/2006 | Collins et al. |
| 7,104,769 B2 | 9/2006 | Davis |
| 7,140,850 B2 | 11/2006 | Otis, Jr. |
| 7,175,649 B2 | 2/2007 | Machold et al. |
| 7,181,927 B2 | 2/2007 | Collins et al. |
| 7,211,106 B2 | 5/2007 | Dobak, III et al. |
| 7,247,165 B2 | 7/2007 | Machold et al. |
| 7,258,662 B2 | 8/2007 | Machold et al. |
| 7,300,264 B2 | 11/2007 | Souza |
| 7,300,453 B2 | 11/2007 | Yon |
| 7,357,786 B1 | 4/2008 | Bakke |
| 7,377,935 B2 | 5/2008 | Schock et al. |
| 7,403,704 B2 | 7/2008 | Eccleston et al. |
| 7,510,569 B2 | 3/2009 | Dae et al. |
| 7,516,909 B2 | 4/2009 | Kaligian, II et al. |
| 7,645,127 B2 | 1/2010 | Hagen et al. |
| 7,658,755 B2 | 2/2010 | Machold et al. |
| 7,666,215 B2 | 2/2010 | Callister et al. |
| 7,713,036 B2 | 5/2010 | Kojima et al. |
| 7,806,915 B2 | 10/2010 | Scott et al. |
| 7,820,102 B2 | 10/2010 | Myrick et al. |
| 7,822,485 B2 | 10/2010 | Collins |
| 7,846,193 B2 | 12/2010 | Dae et al. |
| 7,857,781 B2 | 12/2010 | Noda et al. |
| 7,879,077 B2 | 2/2011 | Machold et al. |
| 7,892,269 B2 | 2/2011 | Collins et al. |
| 7,896,009 B2 | 3/2011 | Stull |
| 7,914,564 B2 | 3/2011 | Magers et al. |
| 7,959,657 B1 | 6/2011 | Harsy |
| 7,963,986 B2 | 6/2011 | Machold et al. |
| 8,038,639 B2 | 10/2011 | Lo et al. |
| 8,047,010 B2 | 11/2011 | Carson et al. |
| 8,061,790 B2 | 11/2011 | Anikhindi et al. |
| 8,105,262 B2 | 1/2012 | Noda et al. |
| 8,105,263 B2 | 1/2012 | Noda et al. |
| 8,105,264 B2 | 1/2012 | Noda et al. |
| 8,109,894 B2 | 2/2012 | Noda et al. |
| 8,128,384 B2 | 3/2012 | Mou |
| 8,177,824 B2 | 5/2012 | Machold et al. |
| 8,226,605 B2 | 7/2012 | Faries, Jr. et al. |
| 8,246,669 B2 | 8/2012 | Machold et al. |

(56) References Cited

U.S. PATENT DOCUMENTS

| | | |
|---|---|---|
| 8,262,716 B2 | 9/2012 | Bleam et al. |
| 8,272,857 B2 | 9/2012 | Norman et al. |
| 8,366,667 B2 | 2/2013 | Chan et al. |
| 8,397,769 B2 | 3/2013 | Catelli |
| 8,551,151 B2 | 10/2013 | Machold et al. |
| 8,740,959 B2 | 6/2014 | Machold et al. |
| 8,784,464 B2 | 7/2014 | Machold et al. |
| 8,808,344 B2 | 8/2014 | Scott et al. |
| 8,888,729 B2 | 11/2014 | Noda et al. |
| 9,233,193 B2 | 1/2016 | Truckai et al. |
| 9,237,919 B2 | 1/2016 | Maschke |
| 9,289,541 B2 | 3/2016 | Norman et al. |
| 9,314,370 B2 | 4/2016 | Dabrowiak et al. |
| 9,345,614 B2 | 5/2016 | Schaefer et al. |
| 9,474,644 B2 | 10/2016 | Dabrowiak |
| 9,492,633 B2 | 11/2016 | Dabrowiak |
| 9,522,080 B2 | 12/2016 | Collins et al. |
| 9,610,392 B2 | 4/2017 | Farrell et al. |
| 9,675,756 B2 | 6/2017 | Kamen et al. |
| 9,777,720 B2 | 10/2017 | Gledhill, III et al. |
| 9,784,263 B2 * | 10/2017 | Hendricks ............ F04B 43/1253 |
| 9,844,460 B2 | 12/2017 | Weber et al. |
| 10,022,265 B2 | 7/2018 | Pamichev et al. |
| 10,035,486 B2 | 7/2018 | Oh |
| 10,085,880 B2 | 10/2018 | Machold et al. |
| 10,206,735 B2 | 2/2019 | Kaveckis et al. |
| 10,368,912 B2 | 8/2019 | Truckai et al. |
| 10,369,267 B2 | 8/2019 | Norman et al. |
| 10,561,528 B2 | 2/2020 | Mazzone et al. |
| 10,758,406 B2 | 9/2020 | Mazzone et al. |
| 10,858,802 B2 | 12/2020 | Bath et al. |
| 11,116,657 B2 | 9/2021 | Dabrowiak et al. |
| 11,123,221 B2 | 9/2021 | Dabrowiak et al. |
| 11,185,440 B2 | 11/2021 | Dabrowiak et al. |
| 11,253,392 B2 | 2/2022 | Dabrowiak et al. |
| 2001/0031946 A1 | 10/2001 | Walker et al. |
| 2002/0004675 A1 | 1/2002 | Lasheras |
| 2002/0022823 A1 | 2/2002 | Luo et al. |
| 2002/0117559 A1 | 8/2002 | Kaligain |
| 2002/0183692 A1 | 12/2002 | Callister |
| 2003/0062090 A1 | 4/2003 | Secondo |
| 2003/0135252 A1 | 7/2003 | MacHold |
| 2003/0036496 A1 | 12/2003 | Samson et al. |
| 2004/0026068 A1 | 2/2004 | Schmidt et al. |
| 2004/0089058 A1 | 5/2004 | De Haan et al. |
| 2004/0171935 A1 | 9/2004 | Van Creveld et al. |
| 2004/0210231 A1 | 10/2004 | Boucher et al. |
| 2004/0267340 A1 | 12/2004 | Cioanta et al. |
| 2005/0047925 A1 | 3/2005 | Davis |
| 2005/0065584 A1 | 3/2005 | Schiff et al. |
| 2005/0069437 A1 | 3/2005 | Mittelstein |
| 2005/0156744 A1 | 7/2005 | Pires |
| 2006/0064146 A1 | 3/2006 | Collins |
| 2006/0069418 A1 | 3/2006 | Schock et al. |
| 2006/0210424 A1 | 9/2006 | Mallett et al. |
| 2006/0241335 A1 | 10/2006 | Benkowski et al. |
| 2006/0293734 A1 | 12/2006 | Scott et al. |
| 2007/0007640 A1 | 1/2007 | Harnden et al. |
| 2007/0076401 A1 | 4/2007 | Carrez et al. |
| 2007/0156006 A1 | 7/2007 | Smith |
| 2007/0191690 A1 | 8/2007 | Hasse et al. |
| 2008/0230530 A1 | 9/2008 | Augustine et al. |
| 2008/0262409 A1 | 10/2008 | Derrico et al. |
| 2008/0267599 A1 | 10/2008 | Arnold et al. |
| 2009/0065565 A1 | 3/2009 | Cao |
| 2009/0099518 A1 | 4/2009 | Magers |
| 2009/0160297 A1 | 6/2009 | Anikhindi |
| 2009/0206778 A1 | 8/2009 | Roh |
| 2010/0036486 A1 | 2/2010 | Mazur |
| 2010/0129248 A1 | 5/2010 | Mou |
| 2010/0204765 A1 | 8/2010 | Hall et al. |
| 2011/0022136 A1 | 1/2011 | Scott et al. |
| 2011/0046551 A1 | 2/2011 | Augustine et al. |
| 2011/0184253 A1 | 7/2011 | Archer et al. |
| 2011/0208276 A1 | 8/2011 | Machold et al. |
| 2011/0208278 A1 | 8/2011 | Machold et al. |
| 2011/0213305 A1 | 9/2011 | Jonsson et al. |
| 2012/0100023 A1 | 4/2012 | Hanazuke |
| 2012/0148415 A1 | 6/2012 | Brueckner |
| 2012/0158103 A1 | 7/2012 | Bledsoe |
| 2013/0071270 A1 | 3/2013 | Zupp |
| 2013/0079853 A1 | 3/2013 | Pasche |
| 2013/0098880 A1 | 4/2013 | Korolev et al. |
| 2013/0150929 A1 | 6/2013 | Machold et al. |
| 2013/0178923 A1 | 7/2013 | Dabrowiak |
| 2013/0079855 A1 | 8/2013 | Helkowski |
| 2014/0081202 A1 | 3/2014 | Tsoukalis |
| 2014/0094880 A1 | 4/2014 | Lim |
| 2014/0094882 A1 | 4/2014 | Lim |
| 2014/0094883 A1 | 4/2014 | Lim |
| 2014/0277302 A1 | 9/2014 | Weber et al. |
| 2014/0364928 A1 | 12/2014 | Machold et al. |
| 2015/0314055 A1 | 11/2015 | Hogard et al. |
| 2016/0131127 A1 | 5/2016 | Hendricks |
| 2016/0228291 A1 | 8/2016 | Calliser et al. |
| 2016/0290330 A1 | 10/2016 | Pamichev et al. |
| 2018/0128258 A1 | 5/2018 | Hendricks |
| 2018/0325725 A1 | 11/2018 | Dabrowiak et al. |
| 2019/0133820 A1 | 5/2019 | Jacobsen et al. |

FOREIGN PATENT DOCUMENTS

| | | |
|---|---|---|
| CN | 102338070 | 2/2012 |
| CN | 202942288 | 5/2013 |
| CN | 106068112 | 11/2016 |
| DE | 19531935 | 2/1997 |
| DE | 102009050053 | 5/2011 |
| EP | 0663529 | 7/1995 |
| EP | 1623733 | 8/2007 |
| GB | 1183185 | 3/1970 |
| GB | 2040169 | 8/1980 |
| GB | 2212262 | 7/1989 |
| GB | 2383828 | 7/2003 |
| JP | S61100243 | 5/1986 |
| JP | H06-218042 | 8/1994 |
| JP | 7308338 | 11/1995 |
| JP | H7-286582 | 3/1997 |
| JP | 09-215754 | 8/1997 |
| JP | 10-0127777 | 5/1998 |
| JP | 10-305103 | 11/1998 |
| JP | 2001147095 | 5/2001 |
| JP | 2002534160 | 10/2002 |
| JP | 2003028582 | 1/2003 |
| JP | 2003508150 | 3/2003 |
| JP | 2003524507 | 8/2003 |
| JP | 2004504110 | 2/2004 |
| JP | 2005-083378 | 3/2005 |
| JP | 2007-507637 | 3/2007 |
| JP | 2008154751 | 7/2008 |
| JP | 2008531114 | 8/2008 |
| JP | 2008539034 | 11/2008 |
| JP | 2009500066 | 1/2009 |
| JP | 2011505929 | 3/2011 |
| JP | 2011137621 | 7/2011 |
| JP | 2011182849 | 9/2011 |
| JP | 2013519849 | 5/2013 |
| JP | 2014023604 | 2/2014 |
| JP | 2017508509 | 3/2017 |
| JP | 2017511716 | 4/2017 |
| WO | 1990001682 | 2/1990 |
| WO | 1993002730 | 2/1993 |
| WO | 1993004727 | 3/1993 |
| WO | 1994000177 | 1/1994 |
| WO | 1994001177 | 1/1994 |
| WO | 9503680 | 2/1995 |
| WO | 1997025011 | 7/1997 |
| WO | 1998024491 | 6/1998 |
| WO | 1998040017 | 9/1998 |
| WO | 2000010494 | 3/2000 |
| WO | 2001013809 | 3/2001 |
| WO | 0126719 | 4/2001 |
| WO | 2001026719 | 4/2001 |
| WO | 2001064146 | 9/2001 |
| WO | 2001076517 | 10/2001 |

(56) References Cited

FOREIGN PATENT DOCUMENTS

| WO | 2001083001 | 11/2001 |
| WO | 2005117546 | 12/2005 |
| WO | 2006036585 | 4/2006 |
| WO | 2009056640 | 5/2009 |
| WO | 20120175089 | 12/2012 |
| WO | 2014160422 | 10/2014 |
| WO | 2015122938 | 8/2015 |

OTHER PUBLICATIONS

F.W. Behmann, E. Bontke, "Intravasive Kuhlung", Pflugers Archiv, Bd. 263, S. 145-165, 1956.

Wilhelm Behringer, et al., "Rapid Hypothermic Aortic Flush Can Achieve Survival without Brain Damage after 30 Minutes Cardiac Arrest in Dogs", Anesthesiology, V. 93, No. 6, Dec. 2000.

Dorraine Day Watts, et al., "Hypothermic Coagulopathy in Trauma: Effect of Varying Levels of Hypothermia on Enzyme Speed, Platelet Function, and Fibrinolytic Activity", The Journal of Trauma: Injury, Infection and Critical Care, vol. 44, No. 5, 1998.

American Urethane Inc., "Polyurethane Properties", available Oct. 12, 2010, http://web.archive.org/web/20101012211957/http://americanurethane.com/polyurethane-properties.html.

Extra Packaging Corp, Polyurethane Properties and Characteristics, accessed May 9, 2016 at http://www.extrapackaging.com/polyurethane/properties.php.

European Search Report for European Patent Application No. 22159271.0, 6 pages.

Japanese Notice of Reasons for Rejection received for Japanese patent application No. 2020-162702 on Jun. 30, 2022, 8 pages.

\* cited by examiner

HEAT EXCHANGE SYSTEM FOR PATIENT TEMPERATURE CONTROL WITH EASY LOADING HIGH PERFORMANCE PERISTALTIC PUMP

TECHNICAL FIELD

The present application relates generally to heat exchange systems for patient temperature control with easy loading high performance peristaltic pumps.

BACKGROUND

Patient temperature control systems have been introduced to prevent fever in patients in the neuro ICU due to suffering from sub-arachnoid hemorrhage or other neurologic malady such as stroke. Also, such systems have been used to induce mild or moderate hypothermia to improve the outcomes of patients suffering from such maladies as stroke, cardiac arrest, myocardial infarction, traumatic brain injury, and high intracranial pressure. Examples of intravascular heat exchange catheters are disclosed in U.S. Pat. Nos. 7,914,564, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559, 8,888,729, and USPPs 2013/0178923, 2013/0079855, 2013/0079856, 2014/0094880, 2014/0094882, 2014/0094883, all of which are incorporated herein by reference.

External patient temperature control systems may be used. Such systems are disclosed in U.S. Pat. Nos. 6,827,728, 6,818,012, 6,802,855, 6,799,063, 6,764,391, 6,692,518, 6,669,715, 6,660,027, 6,648,905, 6,645,232, 6,620,187, 6,461,379, 6,375,674, 6,197,045, and 6,188,930 (collectively, "the external pad patents"), all of which are incorporated herein by reference.

In general, in all of the intravascular and external patient temperature control solutions, the temperature of the working fluid flowing through the catheter or pad is regulated by a heat exchange console based on feedback provided by the patient's actual body temperature, typically core body temperature as may be variously measured rectally, esophageally, tympanic ear temperature, blood temperature in, e.g., the vena cava, etc. The working fluid temperature is regulated by thermally coupling the working fluid to heating and/or cooling elements in the console. In many cases, the working fluid is forced in a closed fluid circuit path (including the console and the catheter or pad) by a peristaltic pump acting on tubing, e.g., pump tubing or IV tubing, in the fluid circuit path.

SUMMARY

The following patent applications are hereby incorporated by reference herein in their entirety, Ser. No. 14/534,718, filed Nov. 6, 2014, and Ser. No. 14/676,672, filed concurrently herewith.

As understood herein, peristaltic pumps typically include a rotor for revolving one or more rollers against a tube, e.g., a pump tube or, IV tube, or other type of tubing, to force fluid through the tube by peristalsis, and an arcuate raceway against which the tube is urged by the rollers. The ease by which the tube can be loaded between the rollers and raceway competes with the performance of the pump: an easier to load pump typically has lower performance whereas a higher performance pump (with higher pumping pressure and fluid flow) usually entails more complex loading of the tube. This is because in easy to load pumps, the raceway is typically movable away from the rollers to facilitate easily placing the tube between the rollers and raceway, but higher performance pumps require longer raceways (e.g., greater than 180 degrees of arc) that are generally not movable away from the pump, complicating the task of loading the tube (which for high performance applications is relatively thick and inflexible compared to low performance tubes) between the rollers and raceway.

Accordingly, a pump may have an arcuate raceway having a concave inner surface and a rotor facing the inner surface of the raceway. The rotor is rotatable relative to the raceway, and is translationally mounted relative to the raceway between a pump or operating position, wherein the rotor is spaced from the midpoint a first distance, and a tube load position, wherein the rotor is spaced from the midpoint a second distance greater than the first distance. A rotor motor is coupled to the rotor to rotate the rotor. One or more rollers are arranged on the rotor to contact tubing disposed between the rotor and the raceway at least when the rotor is in the pump position. A loading motor may be coupled to the rotor to move the rotor translationally and/or rotationally between the pump position and the tube load position.

In examples, an operating element such as a button may be provided that is manipulable by a person or controller to energize the loading motor.

In another aspect, a method includes rotating a peristaltic pump rotor relative to a raceway to urge fluid through a tube disposed between the raceway and the rotor, and energizing a loading motor to move the rotor away from the raceway.

In another aspect, a pump assembly has a raceway, a rotor spaced from the raceway, and a rotor motor configured to rotate the rotor to urge fluid through a tube disposed between the raceway and the rotor. A loading motor is coupled to the rotor to move the rotor translationally and/or rotationally relative to the raceway.

The details of the various embodiments described herein, both as to their structure and operation, can best be understood in reference to the accompanying drawings, in which like reference numerals refer to like parts, and in which:

DETAILED DESCRIPTION

Figure 1:
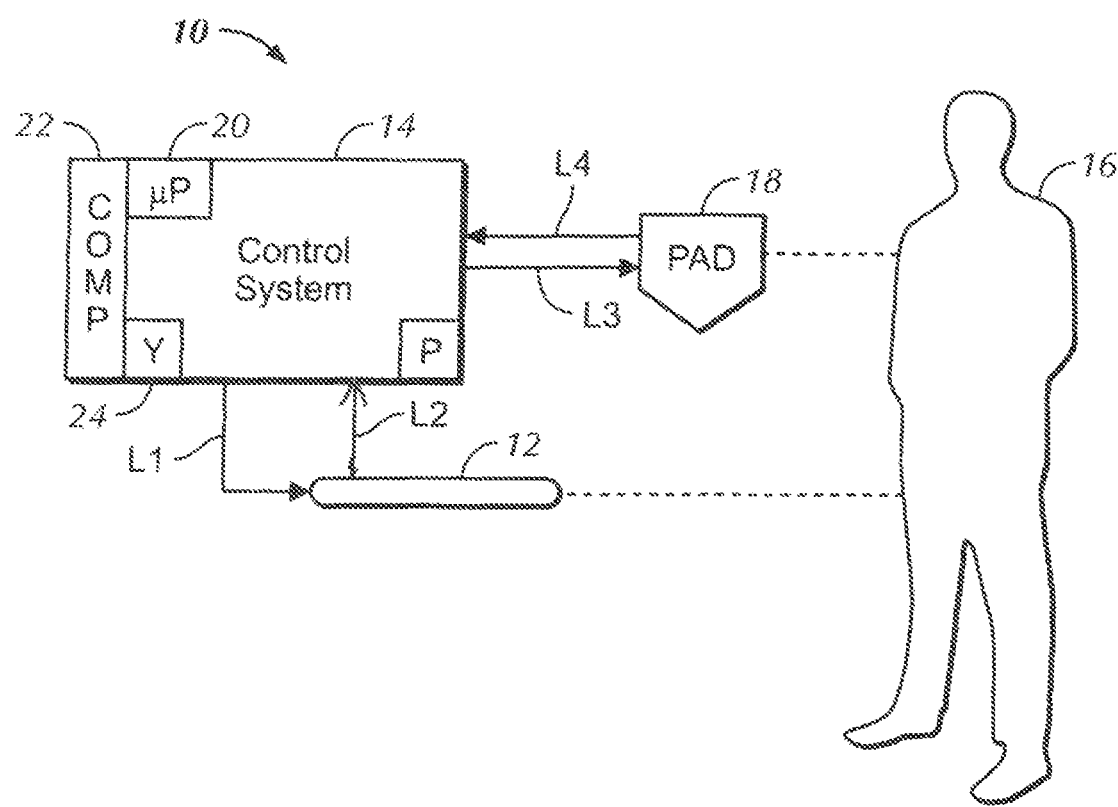
FIG. 1 is a schematic view of a non-limiting system in accordance with an embodiment.

Referring initially to FIG. 1, in accordance with present principles, a system 10 may include an intravascular heat exchange catheter 12 controlled by a control system 14 to control patient temperature, e.g., to prevent the patient 16 from becoming febrile or to induce therapeutic hypothermia in the patient 16. In the catheter, working fluid or coolant such as but not limited to saline circulates (typically under the influence of a pump "P" in the control system) in a closed loop from the control system 14, through a fluid supply line L1, through the catheter 12, and back to the system 14 through a fluid return line L2, such that no working fluid or coolant enters the body. While certain preferred catheters are disclosed herein, it is to be understood that other catheters can be used in accordance with present principles, including, without limitation, any of the catheters disclosed above or in the following U.S. patents, all incorporated herein by reference: U.S. Pat. Nos. 5,486,208, 5,837,003, 6,110,168, 6,149,673, 6,149,676, 6,231,594, 6,264,679, 6,306,161, 6,235,048, 6,238,428, 6,245,095, 6,251,129, 6,251,130, 6,254,626, 6,261,312, 6,312,452, 6,325,818, 6,409,747, 6,368,304, 6,338,727, 6,299,599, 6,287,326, 6,126,684, 7,211,106. The catheter 12 may be placed in the venous system, e.g., in the superior or inferior vena cava.

Instead of or in addition to the catheter 12, the system 10 may include one or more pads 18 that are positioned against the external skin of the patient 16 (only one pad 18 shown for clarity). The pad 18 may be, without limitation, any one of the pads disclosed in the external pad patents. The temperature of the pad 18 can be controlled by the control system 14 to exchange heat with the patient 16, including to induce therapeutic mild or moderate hypothermia in the patient in response to the patient presenting with, e.g., cardiac arrest, myocardial infarction, stroke, high intracranial pressure, traumatic brain injury, or other malady the effects of which can be ameliorated by hypothermia. The pad 18 may receive working fluid from the system 14 through a fluid supply line L3, and return working fluid to the system 14 through a fluid return line L4. The pump "P" may be a peristaltic pump which engages any one of the lines L1-L4, which are typically plastic IV lines, to urge working fluid through the lines through peristalsis.

The control system 14 may include one or more microprocessors 20 receiving target and patient temperatures as input and controlling, among other things, the pump "P" and a refrigerant compressor 22 and/or a bypass valve 24 that can be opened to permit refrigerant to bypass a condenser.

Turning now to FIGS. 2-5, an example of the pump "P" in FIG. 1 is shown and generally designated 30. The pump 30 includes a rigid, preferably metal or hard plastic raceway 32 or channel and a rotor 34. The raceway 32 may be formed from one or more blocks of material as shown and has an inner arcuate surface 36 which may have a substantially constant radius of curvature. In some examples, the arcuate surface 36, which defines a midpoint 38 between its two ends 40, 42 (labeled in FIG. 3), can extend through an arc of at least one hundred eighty degrees (180°) (e.g. where two drive rollers are used) and may extend through an arc of between one hundred eighty degrees (180°) and two hundred seventy degrees (270°). In the example shown, the arcuate surface 36 extends, from one end 40 to the other end 42, through an arc of greater than 200°. For example, the arc may be about 210° to 230°. In certain embodiments, the arcuate surface of a raceway may extend through an arc equal to 360° divided by n, where n is equal to the number of drive rollers mounted on or near a rotor which is rotated relative to the raceway.

Figure 2:
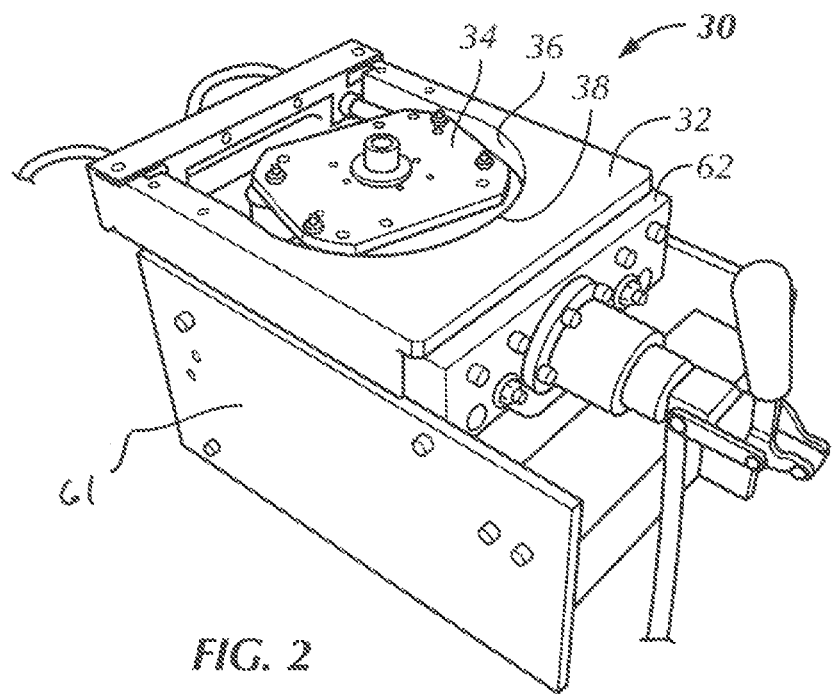
FIG. 2 is a perspective view of the pump with the rotor in the pump position.
Figure 3:
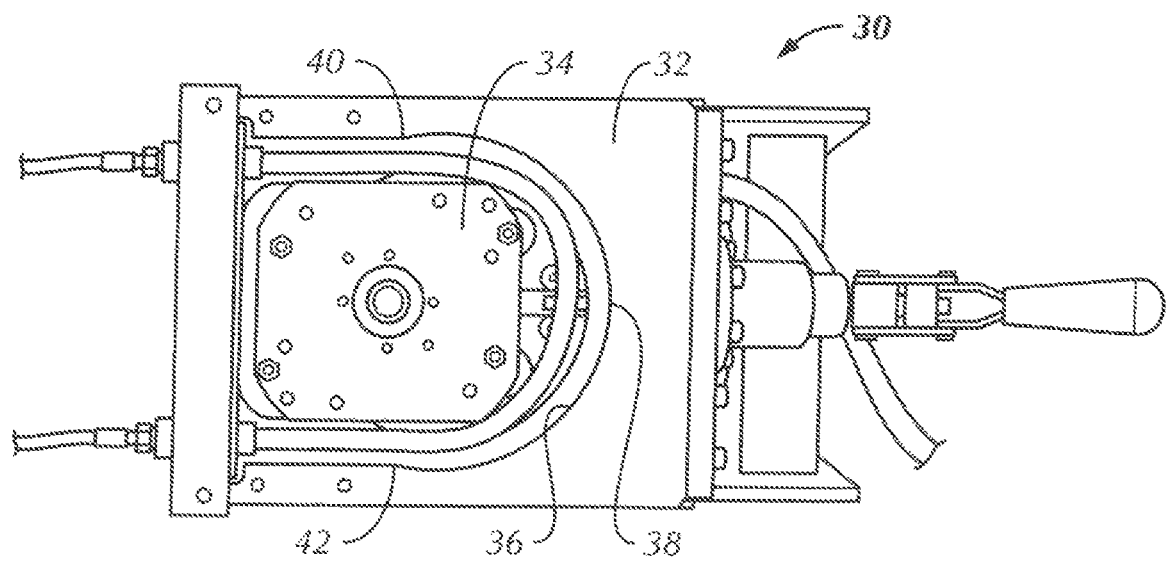
FIG. 3 is a top view of the pump with the rotor in the pump position.
Figure 4:
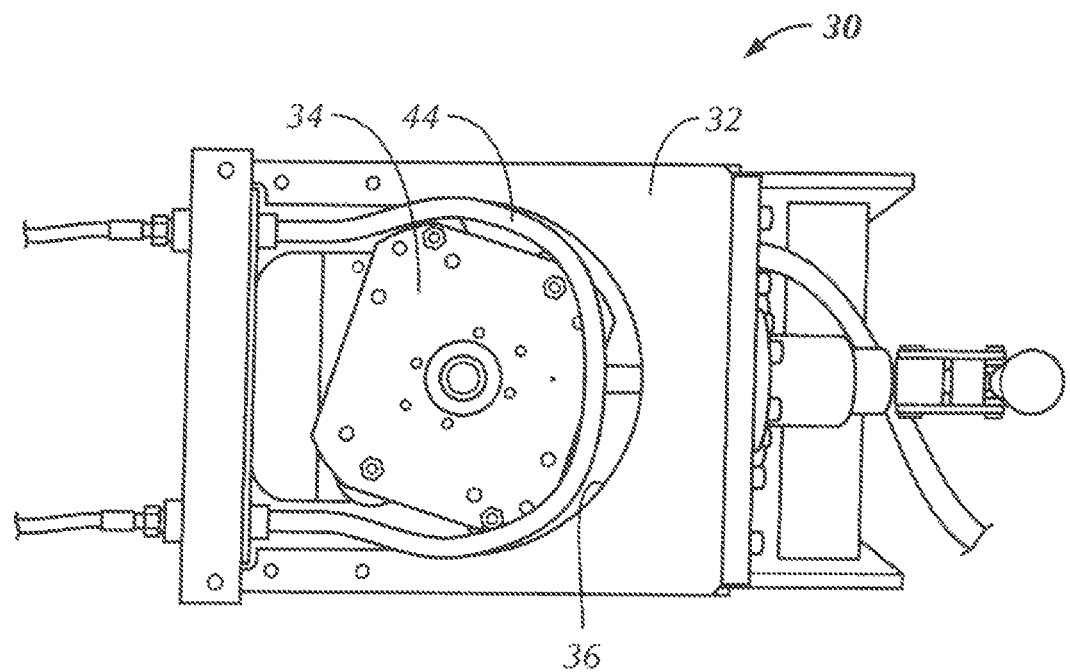
FIG. 4 is a perspective view of the pump with the rotor in the tube load position; illustrating a person manually loading the tube between the raceway and the rotor.
Figure 5:
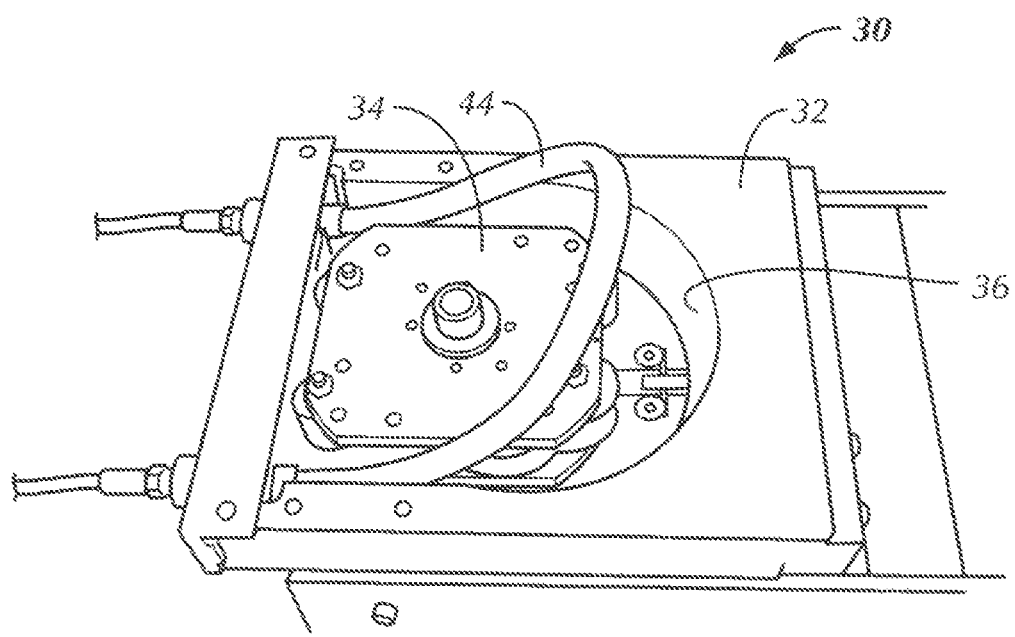
FIG. 5 is a top view of the pump with the rotor in the tube load position.

Covering more than 180° degrees of arc with the raceway may provide additional benefits, such as an extra margin against internal leakage. Furthermore, it is possible that covering more than 180° degrees of arc allows the tubing to open gradually after being compressed by a drive roller and thereby reduce the degree of pulsatility of the flow. This in turn can reduce the amount of unwanted movement experienced by the downstream tubing and catheter when subject to pulsating flow. A motor, described further below, rotates the rotor 34 relative to the raceway 32. As well, the rotor 34 is movable translationally and/or rotationally relative to the raceway 32 between a pump position (FIGS. 2, 3, 6, 7, and 9), in which the rotor 34 is spaced from the midpoint 38 of the inner surface 36 of the raceway 32 a first distance, and a tube load position (FIGS. 4, 5, and 8), in which the rotor 34 is spaced from the midpoint 38 a greater, second distance. As shown in FIGS. 2 and 3, in the pump position, rollers on the rotor 34 urge against a tube such as a pump tube or IV tube that is disposed between the rollers and the raceway 32. In the tube load position, the rotor 34 is sufficiently spaced from the raceway 32 to permit a tube 44 to be disposed between the raceway 32 and rotor 34 and to be removed therefrom, e.g., by hand. Example mechanisms for moving the rotor translationally and/or rotationally are discussed further below.

Indeed and now referring to FIGS. 6-9 for example structure, mounted on the rotor 34 are one or more rollers to urge against the tube 44 to pump fluid through the tube. In the example shown in FIG. 6, the rotor 34 is defined in part by a rectilinear, non-square body, and on or near each corner of the body a roller is mounted, e.g., rotatably mounted to the rotor body. In the example, at one set of opposed corners on the body, drive rollers 46 are respectively mounted (only one drive roller shown in the perspective of FIG. 6), whereas at the other set of opposed corners on the body, guide rollers 48 are respectively mounted. Thus, between the drive rollers 46 are guide rollers 48.

Figure 6:
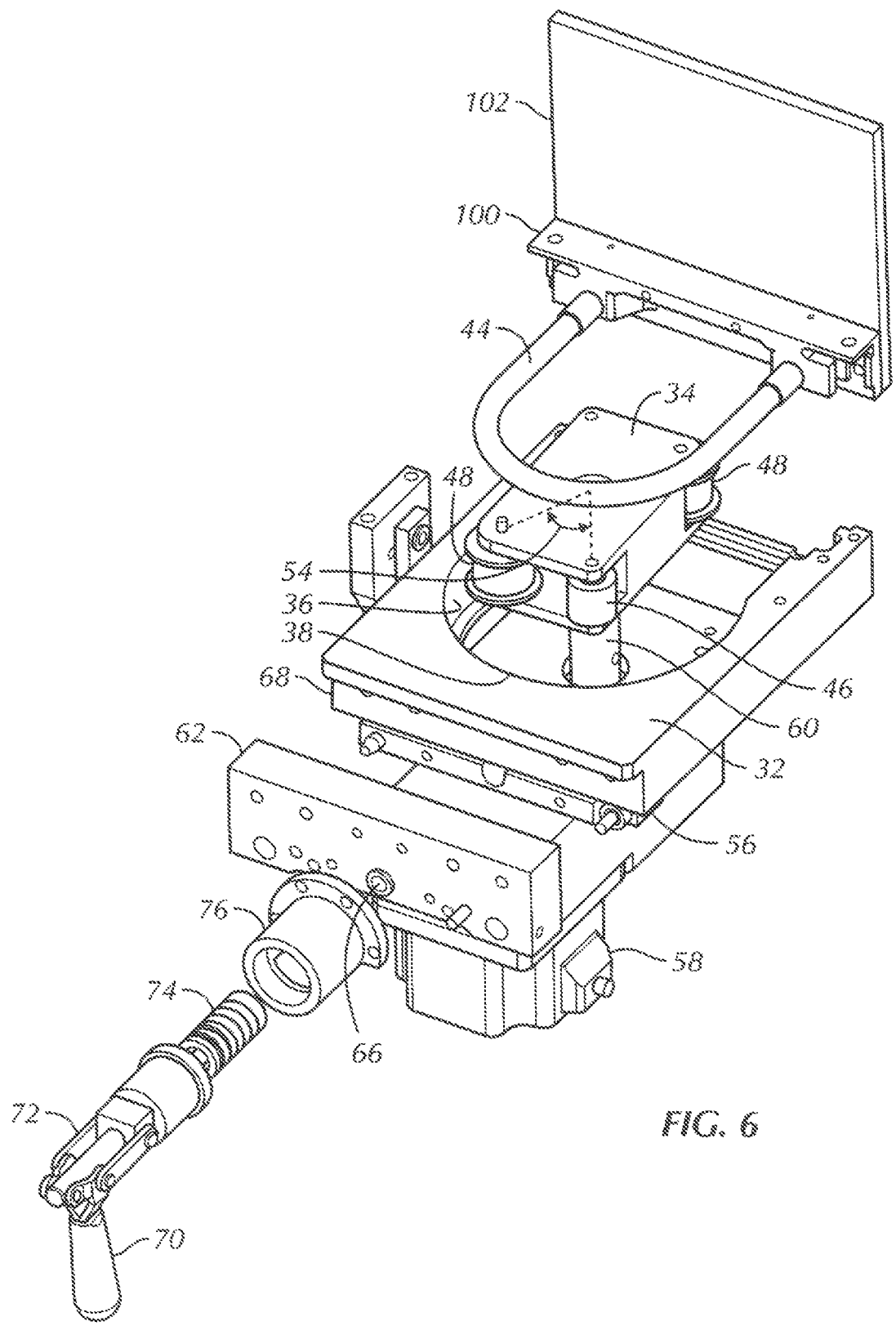
FIGS. 6 and 7 are exploded perspective views from the bottom and top, respectively, of the pump, illustrating features of an example embodiment, with portions broken away in FIG. 7.

As shown in FIG. 6, the drive roller 46 has a cylindrical or similar to cylindrical outer surface, and at least a portion of the outer surface is configured to urge against the tube 44. The outer surface of the example drive roller may be a single smooth cylinder and/or it may or may not have one or more flanges having peripheries extending beyond the cylindrical outer surface. In contrast, FIG. 7 best shows that the guide roller 48 also has a cylindrical (or similar) outer surface but in addition includes top and/or bottom flanges 50, 52 defining respective peripheries extending beyond the cylindrical outer surface of the guide roller such that the tube 44 can be received on the cylindrical outer surface of the guide roller between the flanges 50, 52 when the rotor is in the pump position and is rotated. In the example shown, two and only two drive rollers 46 and two and only two guide rollers 48 are provided, but any number of drive and/or guide rollers may be utilized. In certain embodiments, the drive roller or guide roller may have a non-cylindrical or partially cylindrical outer surface.

Also, in the example shown, owing to the non-square shape of the rotor 34 body, the angle 54 between the drive roller 46 and glide roller 48 at one of the ends of the rotor body, with a vertex on a point on the roller body (e.g., the midpoint), is not ninety degrees. Instead, in the example shown, the angle 54 may be, for example, fifty five degrees. The same angle obtains at the opposite end of the rotor body. However, in some embodiments the rotor body is square, in which case all rollers are separated from the adjacent rollers by ninety degrees.

A block-like motor mount 56 supports a motor 58 such as a small ac or dc motor, in some embodiments, a stepper motor or other appropriate motor type. The motor 58 is coupled to the rotor 34 by an output shaft 60, with, in some embodiments, a reduction gear train (not shown) being meshed between the motor shaft and the output shaft 60.

A positioning mechanism is coupled to the motor mount 56 and is manipulable by a person to move the motor mount 56 to thereby move the rotor 34 between the pump position and the tube load position. In a non-limiting example, referring briefly back to FIG. 2, a base 61 stationarily holds the raceway 32, and a rectilinear rigid support block 62 (FIGS. 2 and 6-9) may be bolted or welded to the base 61 or made integrally therewith. A push rod 64 (FIGS. 7-9) extends through a hole 66 in the support block 62 to contact and/or be engaged with the motor mount 56 and/or with a motor plate 68 coupled to the motor mount 56. A handle 70 is coupled at a hinge mechanism 72 to the push rod 64. The handle 70 can be moved by hand to a substantially perpendicular orientation relative to the push rod 64 (FIGS. 6 and 9) to pull the push rod 64 and thus to move the motor mount 56 (and hence rotor 34) toward the inner surface of the raceway 32, thereby moving the rotor 34 to the pump position. The handle 70 can also be moved by hand down from the perpendicular orientation to the non-perpendicular orientation shown in FIGS. 7 and 8. This pushes the push rod 64 and thus moves the motor mount 56/rotor 34 away from the pump position to the tube load position. One or more radial bearings 74, 76 may be provided as appropriate to radially support elements of the positioning mechanism.

Figure 7:
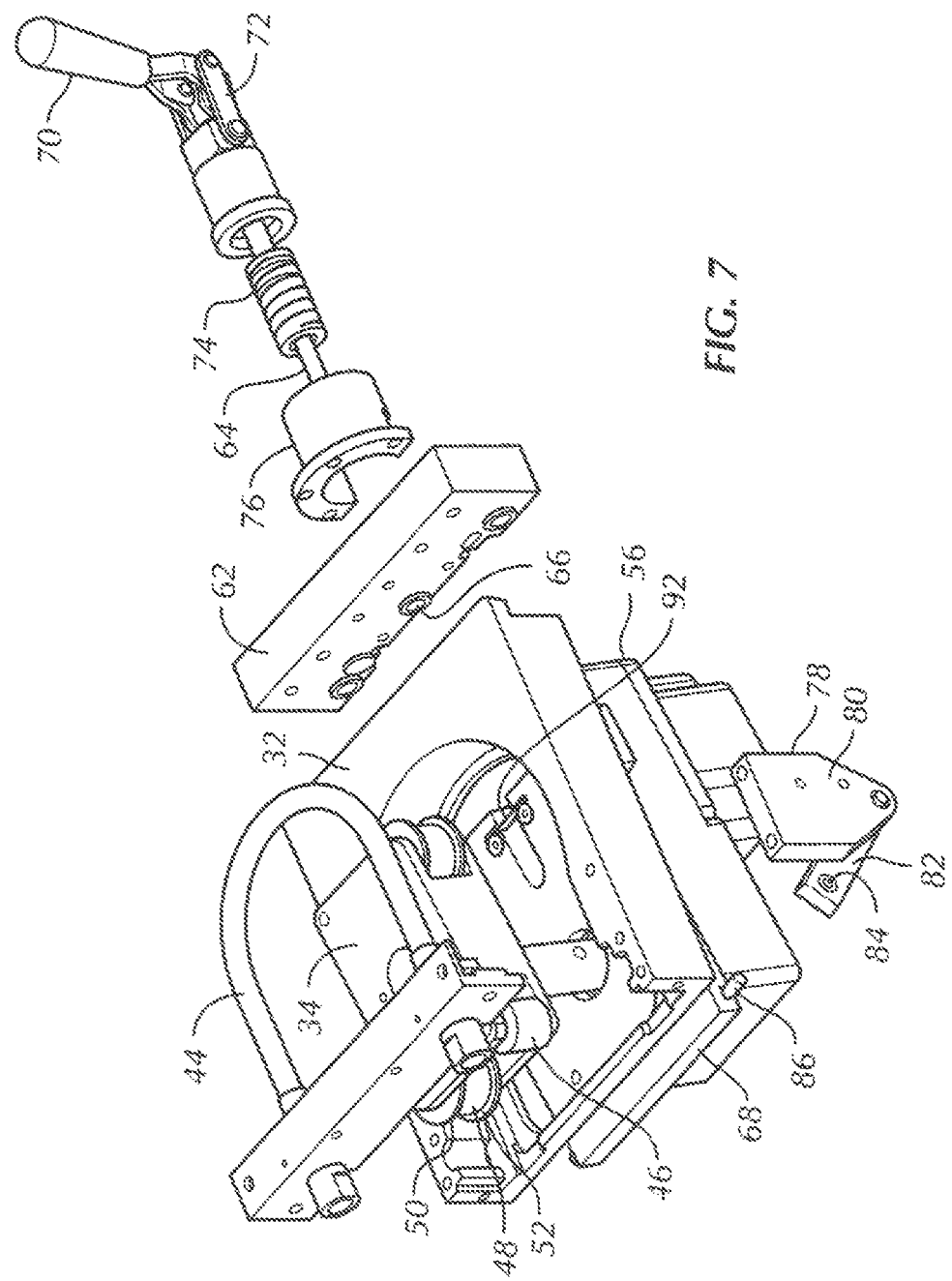

Also and focusing on FIG. 7, to support the motor mount 56 and attendant elements that move with it, two side brackets 78 may be provided on respective sides of the raceway 32 (only one bracket 78 shown in FIG. 7). A vertical flange 80 of the side bracket 78 may be affixed to the raceway 32, e.g., by threaded fasteners or welding, and a swing arm 82 pivotably coupled to the vertical flange 80 and rotatably coupled to the motor mount 56 or other component that moves with the motor mount 56. In the example shown in FIG. 7, a hole 84 is formed in the swing arm 82 and rotatably engages a pin 86 that is attached to and that extends radially away from the motor plate 68. Recall that the motor mount 56, motor plate 68, and rotor 34 move translationally together as unit.

Figure 8:
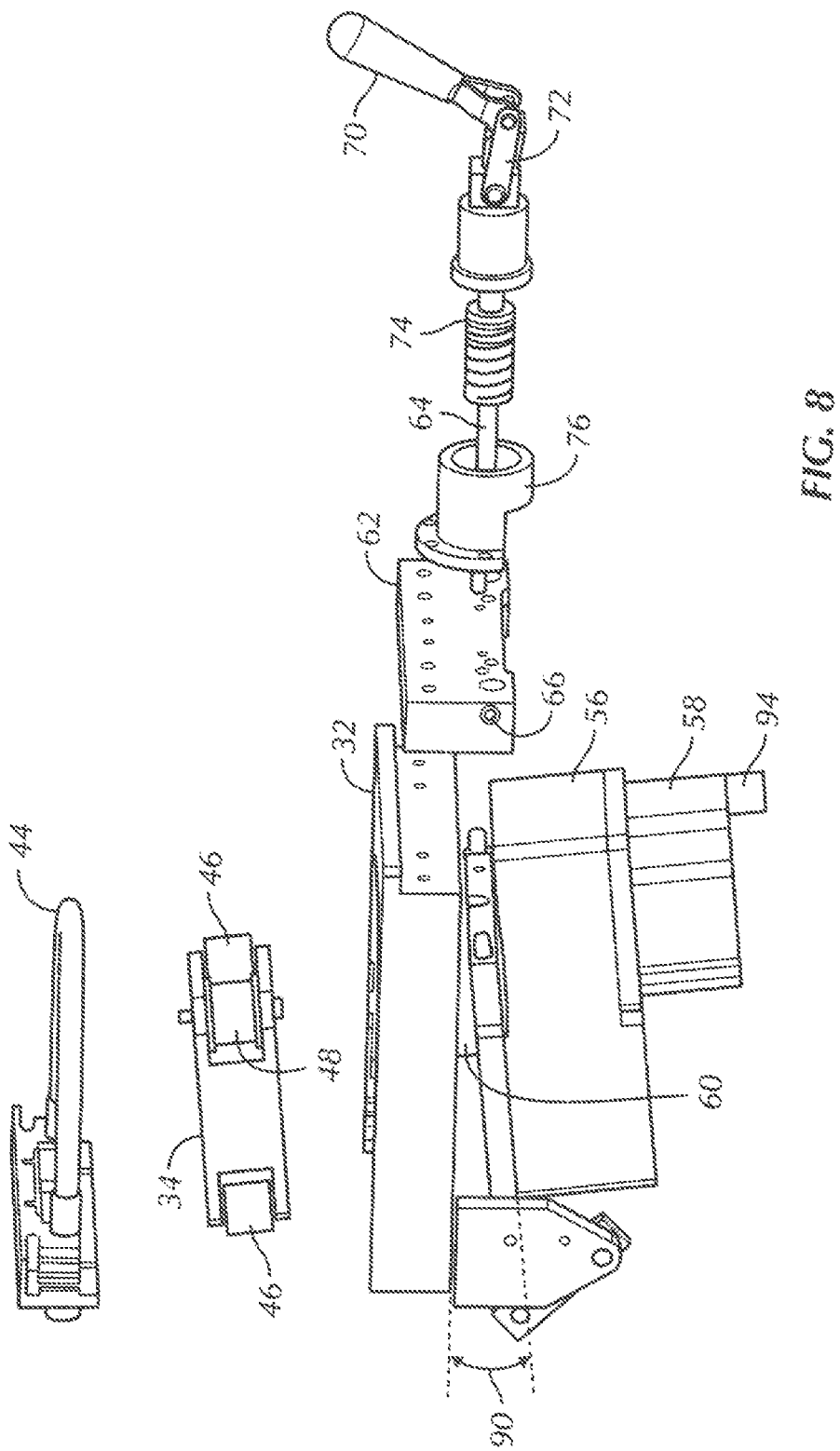
FIGS. 8 and 9 are exploded side views respectively showing the relationship between the motor mount and the raceway in the tube load and pump positions of the rotor, with some portions broken away.
Figure 9:
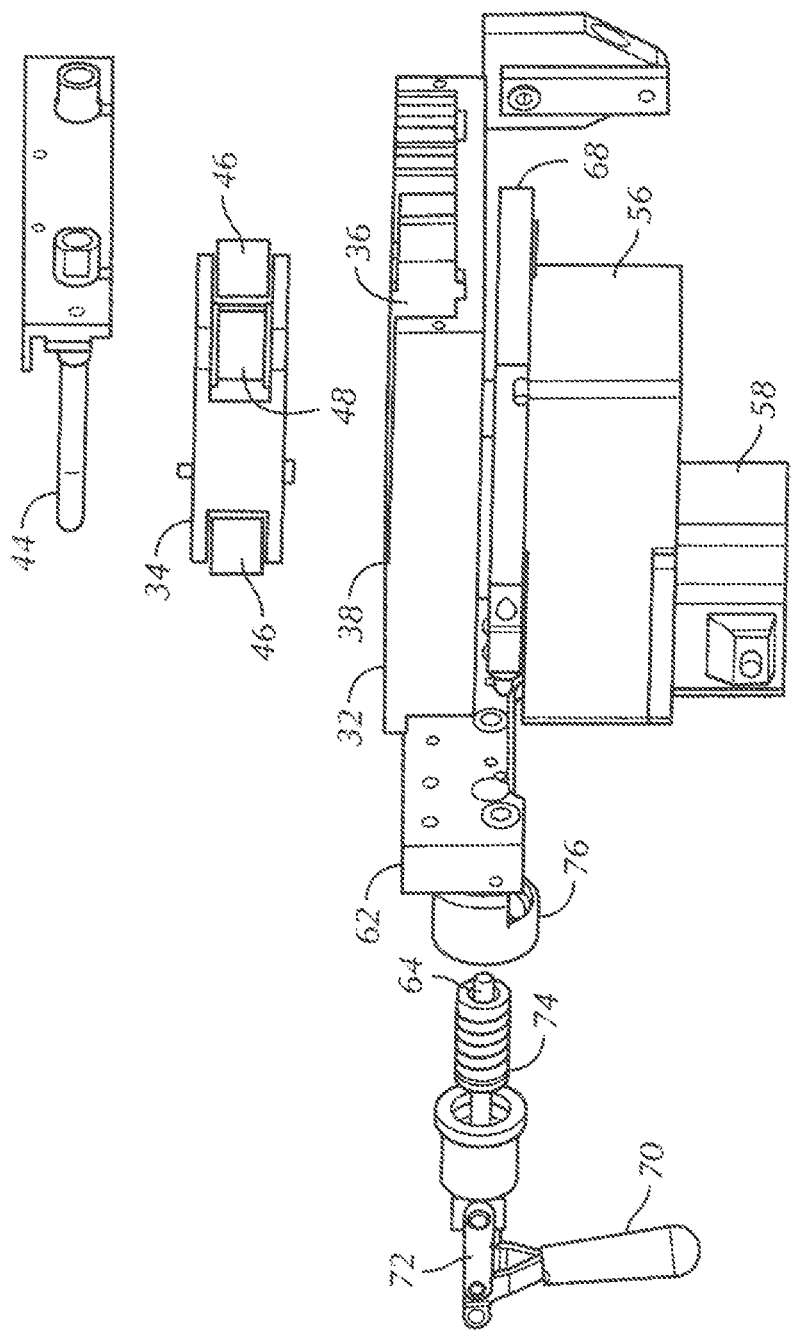

Owing to the example positioning mechanism described above, as best shown in FIG. 9 the motor mount 56 (with motor plate 68) is parallel to the raceway 32 when the rotor 34 is in the pump position. In contrast, as best shown in FIG. 8, the motor mount 56 (with motor plate 68) is obliquely angled relative to the raceway 32 when the rotor 34 is in the tube load position. That is, an oblique angle 90 is established between, for example, the plane of the motor plate 68 and the plane defined by the bottom surface of the raceway 32 when the rotor 34 is in the tube load position. To further facilitate motion of the positioning mechanism when the handle 70 is moved, a hinge pin 92 (FIG. 7) may be provided as part of the coupling between the push rod 64 and motor mount 56/motor plate 68.

Thus, the rotor 34 can move linearly relative to raceway 32. In the example shown, linear bearings are used, it being understood that equivalently a multi-bar linkage between the rotor 34 and raceway 32 can be used for pseudo-linear motion. In any case, in the tube position the rotor 34 is a sufficient distance (typically an inch or more) so that the tube 44 can be inserted freely between the rotor 34 and raceway 32 by a person. Then, when the rotor is moved to the pump position, at least the drive rollers 46 urge into the tube 44 sufficiently to stretch the tube 44 by an elongation of at least 3% and typically 3-15%. This elongation advantageously ensures that slack does not build up in the tubing as it wears and stretches during use. As understood herein, such slack can lead to kinking of the tubing or excessive wear.

FIG. 8 is used to schematically show that at least one angular position sensor 94 can be provided on the motor 58. Without limitation, the angular position sensor may be a Hall effect sensor, or a dc stepper motor revolution counter, or a potentiometer type sensor. The sensor 94 generates an output representative of the angular position of the motor. The sensor 94 may be coupled to the motor shaft or the output shaft 60 or other part of the rotating mechanism in the pump.

In any case, the processor 20 shown in FIG. 1 can control the motor 58 and can receive the signal from the sensor 94. Using the signal from the sensor 94, the processor 20 can prevent the motor 58 from stopping at an angular position corresponding to at least one roller 46/48 being in a predetermined angular location relative to the raceway 32. In an example, the predetermined location of the roller corresponding to the angular position at which the motor is prevented from stopping is at an arc end 40 or 42 of the raceway 32. This ensures that, particularly when a raceway arc of >180 degrees is used, the rollers will not be in the 12 o'clock and 6 o'clock positions (i.e., adjacent to the ends of the arc), which would interfere with the raceway even when the rotor is in the tube load position and thereby complicate tube loading and unloading.

Thus, the position sensor 94 can be coupled to the motor shaft to indicate critical angular positions to avoid stopping the motor at these positions. The processor 20 can control the motor so that it will not stop on these critical positions. Alternately, the signal from the one or more sensors 94 can be used to indicate non-critical positions, with the processor 20 controlling the motor so it will always stop on these non-critical angular positions. Yet again, a mechanical means, mechanism or other element, e.g., a pin, may be used to ensure that the motor/rotor does not stop in critical positions.

Completing the description, the tube 44 may be configured as a loop as best shown in FIG. 6, with the ends of the loop engaged with a manifold 100 in fluid communication with the interior of the manifold 10. In turn, the interior of the manifold 100 may communicate with a cassette 102 such as the cassette shown and described in U.S. patent application Ser. No. 14/180,655, filed Feb. 24, 2014 and incorporated herein by reference. Such a cassette can be engaged with structure in the control system 14 to exchange heat with working fluid flowing through the cassette 102 and tube 44 and being circulated by the pump 30 shown and described herein to and from a heat exchange member such as the catheter 12 and/or pad 18.

Figure 10:
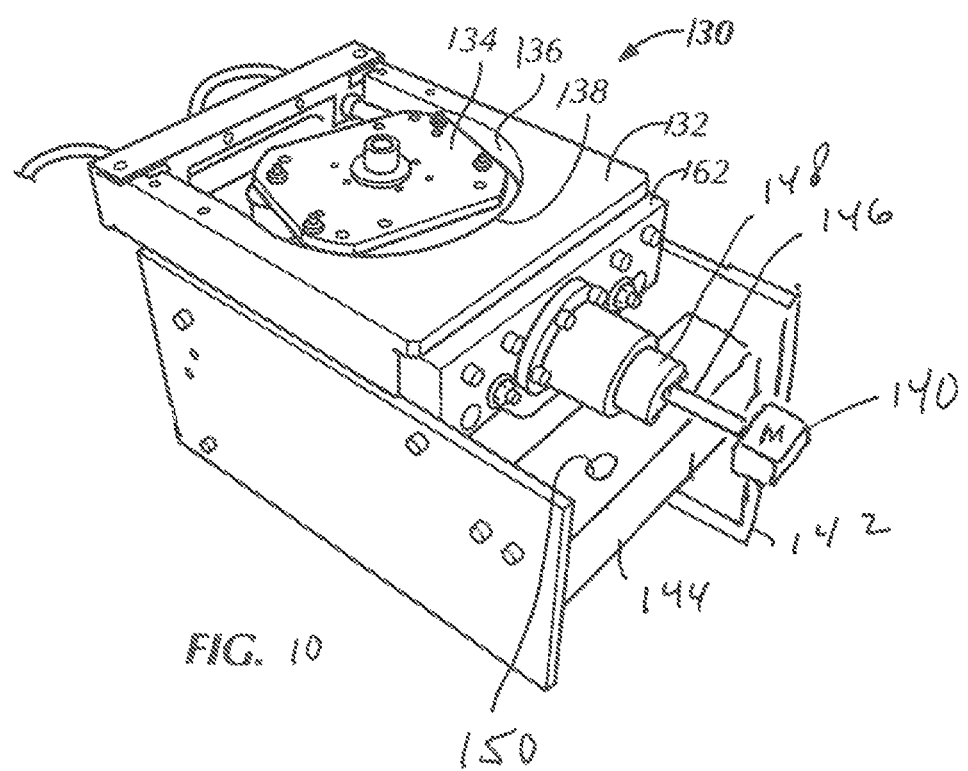
FIG. 10 is a perspective view of an alternate embodiment using a motor instead of a manually-operated handle with the rotor in the pump position, schematically illustrating the motor, gear, and operating button.

FIG. 10 shows an alternate embodiment 130 of the peristaltic pump that in all essential respects is identical in configuration and operation to the pump 30 described above with the exceptions noted. Like the pump 30, the pump 130 in FIG. 10 includes a rigid, preferably metal or hard plastic raceway 132 and a rotor 134. The raceway 132 or channel may be formed from one or more blocks of material as shown and has an inner arcuate surface 136 which may have a substantially constant radius of curvature. The arcuate surface 136 of FIG. 10 is substantially identical in configuration and operation to the arcuate surface 32 in FIG. 2. A motor rotates the rotor 134 relative to the raceway 132. As well, like the rotor 32 shown in FIG. 2, the rotor 134 shown in FIG. 10 may be movable translationally and/or rotationally relative to the raceway 132 between a pump position, in which the rotor 134 is spaced from the midpoint 138 of the inner surface 136 of the raceway 132 a first distance, and a tube load position in which the rotor 134 is spaced from the midpoint 138 a greater, second distance.

However, unlike the pump 30 shown in FIG. 2, the pump 130 shown in FIG. 10 provides a loading motor 140 to provide for automated or automatic movement of the rotor relative to the raceway, e.g., translational or rotational, instead of a manually-manipulable handle. Thus, the pump 130 in FIG. 10 omits, e.g., the handle 10 with hinge mechanism 72.

Instead, the loading motor 140, which may be mounted (e.g., directly on or by means of a bracket 142) to a pump base 144, reciprocatingly drives a push rod 146 to move the rotor 134 between the pump position and tube load position. Advantages associated with using a loading motor to move the rotor include but are not limited to the following: providing convenience for the customer, e.g., the customer may not have to reach back and apply force to move the motor; the customer may not have access to moving parts; minimal or no room for the customer's hand may be needed, which in turn saves space; movement of the rotor may be controlled or allowed only when certain other conditions are met; the rotor may be moved with constant speed; and the force needed to move the rotor may be monitored. The motor 140 may be a direct current (dc) stepper motor or other ac or dc motor, or other appropriate motor type and the push rod 146 may be the rack element of a rack-and-pinion gear, with the pinion portion being geared to a shaft rotated by the motor 140. The push rod 146 may extend through a support block 162 that is substantially identical in configuration and operation to the support block 62 shown in FIG. 6 to contact and/or be engaged with a motor mount that supports the motor that rotates the rotor 134. One or more radial bearings 148 may be provided as appropriate to radially support elements of the positioning mechanism.

An operating button or key 150 may be manipulable by a person or controller to energize the loading motor 140. The button or key 150 may be positioned on the pump 130 base as shown and may be electrically connected to the controller of the motor 140, with the motor and its controller enclosed in the rectangular box shown at 140. In all other essential respects the pump 130 shown in FIG. 10 may be substantially identical in configuration and operation to the pump 30 shown in FIGS. 2-9.

Components included in one embodiment can be used in other embodiments in any appropriate combination. For example, any of the various components described herein and/or depicted in the Figures may be combined, interchanged or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

While various embodiments of HEAT EXCHANGE SYSTEMS FOR PATIENT TEMPERATURE CONTROL WITH EASY LOADING HIGH PERFORMANCE PERISTALTIC PUMPS are herein shown and described in detail, the scope of the present invention is to be limited by nothing other than the appended claims.

What is claimed is:

1. A patient temperature control system comprising:
an intravascular heat exchange catheter;
a tube in fluid communication with the intravascular heat exchange catheter and forming a closed loop; and
a pump assembly configured to urge a working fluid through the tube, the pump assembly comprising:
a raceway; and
a rotor rotatable relative to the raceway, the tube interposed between the rotor and the raceway, wherein the rotor is movable between a first position, in which, the rotor operatively engages the tube against the raceway to urge the working fluid through the tube, and a second position, in which, the rotor is pivotably displaced from the raceway to create a space between the rotor and the raceway in order to provide access to the tube, wherein the raceway is stationary with respect to the pump assembly during loading and unloading of the tube in the raceway.

2. The patient temperature control system according to claim 1, wherein the raceway includes an arcuate portion having opposing arc ends, the tube being looped along the arcuate portion of the raceway.

3. The patient temperature control system according to claim 2, wherein the rotor has a rectangular shape having rounded corners.

4. The patient temperature control system according to claim 3, wherein the rounded corners of the rotor are displaced from the opposing arc ends of the arcuate portion of the raceway when the rotor is in the second position.

5. The patient temperature control system according to claim 3, wherein the pump assembly further includes a roller disposed in one of the rounded corners of the rotor, the roller operatively engaging the tube against the arcuate portion of the raceway to urge the working fluid through the tube.

6. The patient temperature control system according to claim 5, wherein the roller of the rotor and a portion of the arcuate portion of the raceway define a first gap when the rotor is in the first position, and the roller and the portion of the arcuate portion of the raceway define a second gap larger than the first gap when the rotor is in the second position.

7. The patient temperature control system according to claim 2, wherein the arcuate portion of the raceway defines an angle between about 210 degrees and about 230 degrees.

8. The patient temperature control system according to claim 1, wherein the pump assembly further includes an angular position sensor to determine angular orientation of the rotor, the angular position sensor generating an output corresponding to the angular orientation of the rotor.

9. The patient temperature control system according to claim 8, further comprising a controller including a processor configured to receive the output of the angular position sensor and to stop the rotor at a predetermined angular orientation.

10. The patient temperature control system according to claim 1, further comprising a cassette in fluid communication with the tube, the cassette configured to transfer heat from the working fluid flowing through the cassette and the tube and being circulated by the pump assembly.

11. A patient temperature control system comprising:
an intravascular heat exchange catheter;
a tube in fluid communication with the intravascular heat exchange catheter; and
a pump assembly configured to circulate a working fluid through the tube, the pump assembly comprising:
a raceway including an arcuate portion including opposing arc ends; and a rotor rotatable relative to the raceway and including a roller, the tube interposed between the rotor and the arcuate portion of the raceway;

wherein the rotor is movable between a first position, in which, the roller of the rotor operatively engages the tube against the raceway to urge the working fluid through the tube, and a second position, in which the roller is offset from the opposing arc ends of the arcuate portion of the raceway to inhibit obstruction of a gap defined between the rotor and the opposing arc ends of the raceway to facilitate loading and unloading of the tube.

12. The patient temperature control system according to claim 11, wherein the roller of the rotor and a portion of the arcuate portion of the raceway define a first gap when the rotor is in the first position, and the roller and the portion of the arcuate portion of the raceway define a second gap larger than the first gap when the rotor is in the second position.

13. The patient temperature control system according to claim 11, wherein the arcuate portion of the raceway defines an angle between about 180 degrees and about 270 degrees.

14. The patient temperature control system according to claim 13, wherein the angle of the arcuate portion of the raceway is between about 210 degrees and about 230 degrees.

15. The patient temperature control system according to claim 11, wherein the roller of the rotor has a cylindrical profile.

16. The patient temperature control system according to claim 11, wherein the roller of the rotor includes opposing flanges to guide the tube between the opposing flanges when the rotor in the first position is rotated.

17. The patient temperature control system according to claim 11, wherein the tube is stretched when the rotor is in the first position.

18. The patient temperature control system according to claim 11, further comprising a controller including a processor configured to stop the rotor at a predetermined angular orientation.

19. The patient temperature control system according to claim 18, wherein the pump assembly further includes an angular position sensor to determine an angular orientation of the rotor, the angular position sensor generating an output corresponding to the angular orientation of the rotor and being received by the processor of the controller.

20. The patient temperature control system according to claim 11, further comprising a cassette in fluid communication with the tube, the cassette configured to transfer heat from the working fluid flowing through the cassette and the tube and being circulated by the pump assembly.

21. The patient temperature control system according to claim 11, wherein the rotor has a rectangular shape having rounded corners, the rounded corners of the rotor being displaced from the opposing arc ends of the arcuate portion of the raceway when the rotor is in the second position.

* * * * *